United States Patent
Stewart et al.

(10) Patent No.: US 10,918,301 B2
(45) Date of Patent: *Feb. 16, 2021

(54) MULTIPLE RHYTHM TEMPLATE MONITORING

(71) Applicant: Boston Scientific Scimed Inc., Maple Grove, MN (US)

(72) Inventors: Brian Stewart, North Reading, MA (US); Ruslan R. Hristov, Lexington, MA (US)

(73) Assignee: Boston Scientific Scimed Inc., Maple Grove, MN (US)

(*) Notice: Subject to any disclaimer, the term of this patent is extended or adjusted under 35 U.S.C. 154(b) by 20 days.

This patent is subject to a terminal disclaimer.

(21) Appl. No.: 16/364,522

(22) Filed: Mar. 26, 2019

(65) Prior Publication Data

US 2019/0216355 A1 Jul. 18, 2019

Related U.S. Application Data

(63) Continuation of application No. 15/275,381, filed on Sep. 24, 2016, now Pat. No. 10,271,757.

(60) Provisional application No. 62/233,339, filed on Sep. 26, 2015.

(51) Int. Cl.
| | | |
|---|---|---|
| *A61B 5/0452* | (2006.01) | |
| *A61B 5/04* | (2006.01) | |
| *A61B 5/042* | (2006.01) | |
| *A61B 5/044* | (2006.01) | |
| *A61B 5/0432* | (2006.01) | |
| *A61B 5/00* | (2006.01) | |
| *A61B 5/0245* | (2006.01) | |

(52) U.S. Cl.
CPC ........ *A61B 5/04525* (2013.01); *A61B 5/0245* (2013.01); *A61B 5/044* (2013.01); *A61B 5/04012* (2013.01); *A61B 5/0422* (2013.01); *A61B 5/0432* (2013.01); *A61B 5/0452* (2013.01); *A61B 5/6852* (2013.01); *A61B 5/7203* (2013.01); *A61B 5/7221* (2013.01); *A61B 5/7246* (2013.01); *A61B 5/7264* (2013.01); *A61B 5/7475* (2013.01); *A61B 2505/05* (2013.01)

(58) Field of Classification Search
CPC .......................... A61B 5/04525; A61B 5/0245
USPC ........................................................ 600/523
See application file for complete search history.

*Primary Examiner* — Nadia A Mahmood
(74) *Attorney, Agent, or Firm* — Faegre Drinker Biddle & Reath LLP (57) ABSTRACT

A system for providing information about a patient's heart includes one or more electrodes that receive signals from electrical activity of the heart over one or more heart beat cycles. The system is characterized by an electronic processor coupled to the one or more electrodes to: receive the signals from the one or more electrodes; execute an automated set-up routine that processes the signals to automatically provide at least some set-up results for new mapping configurations; and/or process the signals with beat detection and beat acceptance criteria for new or existing mapping configurations to provide information about how well the signals match one or more of the new or existing mapping configurations.

20 Claims, 4 Drawing Sheets

MULTIPLE RHYTHM TEMPLATE MONITORING

CROSS-REFERENCE TO RELATED APPLICATION

This application is a Continuation Application of U.S. patent application Ser. No. 15/275,381, filed Sep. 24, 2016, which claims priority to Provisional Application No. 62/233, 339, filed Sep. 26, 2015, which is herein incorporated by reference in its entirety.

TECHNICAL FIELD

This disclosure relates to systems and methods for providing information about a patient's heart and, in particular, to systems and methods for monitoring and electro-anatomically mapping the patient's heart.

BACKGROUND

Use of minimally invasive procedures, such as catheter ablation, to treat a variety of heart conditions, such as supraventricular and ventricular arrhythmias, is becoming increasingly prevalent. Often, these procedures involve the mapping of electrical activity in the heart at various locations on the endocardium surface, referred to as cardiac mapping, to identify the mechanism of the arrhythmia followed by a targeted ablation. To perform the cardiac mapping, a catheter with one or more electrodes can be inserted into the patient's heart chamber.

Cardiac mapping techniques include contact mapping, near-contact mapping, and non-contact mapping. In contact mapping, one or more catheters are advanced into the heart and physiological signals resulting from the electrical activity of the heart are acquired with one or more electrodes located at the catheter distal tip after determining that the tip is in stable and steady contact with the endocardium surface of a heart chamber. The location and electrical activity can be measured on a point-by-point basis at, for example, about 50 to 200 points on the internal surface of the heart to construct an electro-anatomical depiction of the heart. In near-contact mapping, a movable catheter having multiple spatially distributed electrodes is placed in a heart chamber of interest and moved to one or more locations within the chamber of interest, where the electrodes are on or near, such as within millimeters of, the endocardium surface of the heart chamber. Measurements are taken automatically at each of the locations of the catheter, without determining whether the electrodes are in contact with the surface of the heart. These measurements are analyzed to detect the endocardium surface of the heart chamber in the vicinity of the catheter. The location of the catheter, e.g., a location provided by a tracking system, and the measurements from the electrodes are used to reconstruct the chamber anatomy, where, for example, 20,000 measurements may be made to construct an electro-anatomical depiction of the heart. As the tracked catheter is moved inside the chamber, a partial or complete representation of the chamber anatomy can be constructed. In non-contact mapping, a multiple electrode catheter is placed in the heart chamber of interest and the catheter is deployed to assume a three dimensional shape. Using the signals detected by the non-contact electrodes and information on chamber anatomy and relative electrode location, the system calculates and provides physiological information regarding the endocardium surface of the heart chamber. In these cardiac mapping techniques, the generated map may then serve as the basis for deciding on a therapeutic course of action, such as tissue ablation, to alter the propagation of the heart's electrical activity and to restore normal heart rhythm.

While mapping a patient's heart, the patient may present multiple different types of cardiac rhythms, mixed in time, which the user wants to map and/or the patient may present a paced rhythm. Typically, the mapping system is set to capture one type of cardiac rhythm for a current map. If the cardiac rhythm changes, the new type of cardiac rhythm is not added to the current map. To capture signals associated with the new cardiac rhythm type, the mapping system must be reconfigured to an existing cardiac mapping configuration that matches the current cardiac rhythm or the mapping system must be reconfigured to capture the current cardiac rhythm. However, determining whether an existing cardiac mapping configuration can be used for the current cardiac rhythm can be a difficult and time consuming process and programming a new mapping configuration into the mapping system can take anywhere from 10 seconds to more than a minute, either of which may result in lost data and frustration.

SUMMARY

Example 1 is a system for providing information about a patient's heart. The system includes one or more electrodes that receive signals from electrical activity of the heart over one or more heart beat cycles. In some embodiments, the system is characterized by an electronic processor coupled to the one or more electrodes to: receive the signals from the one or more electrodes; execute an automated set-up routine that processes the signals to automatically provide at least some set-up results for new mapping configurations; and process the signals with beat detection and beat acceptance criteria for the new or existing mapping configurations to provide information about how well the signals match one or more of the new or existing mapping configurations. In some embodiments, the system is characterized by an electronic processor coupled to the one or more electrodes to receive the signals from the one or more electrodes and execute an automated set-up routine that processes the signals to automatically provide at least some set-up results for new mapping configurations. In some embodiments, the system is characterized by an electronic processor coupled to the one or more electrodes to receive the signals from the one or more electrodes and process the signals with beat detection and beat acceptance criteria for new or existing mapping configurations to provide information about how well the signals match one or more of the new or existing mapping configurations.

Example 2 is the system of Example 1, wherein the electronic processor executes the automated set-up routine and processes the signals with the beat detection and beat acceptance criteria for the existing mapping configurations in parallel.

Example 3 vis the system of any of Examples 1 and 2, wherein the electronic processor executes the automated set-up routine at one or more of a predetermined time interval, once every heart beat cycle, and once per second.

Example 4 is the system of any of Examples 1-3, wherein the automated set-up routine provides the new mapping configurations in response to changes in the signals.

Example 5 is the system of any of Examples 1-4, wherein the new mapping configurations are updated and displayed while matching the signals to at least one of the existing mapping configurations and displaying the degree of matching between the signals and the at least one of the new or existing mapping configurations.

Example 6 is the system of any of Examples 1-5, wherein information for making a determination about which of the new or existing mapping configurations most closely matches the signals is displayed.

Example 7 is the system of any of Examples 1-6, comprising a user interface for switching from mapping the signals using one of the existing mapping configurations to mapping the signals using another one of the existing mapping configurations or one of the new mapping configurations.

Example 8 is the system of any of Examples 1-7, wherein the electronic processor determines which of the new mapping configurations and the existing mapping configurations are redundant.

Example 9 is the system of any of Examples 1-8, wherein the electronic processor automatically switches from mapping the signals using one of the existing mapping configurations to mapping the signals using another one of the existing mapping configurations or one of the new mapping configurations.

Example 10 is a method for providing information about a patient's heart. The method includes receiving signals from electrical activity of the heart over one or more heart beat cycles at one or more electrodes and is characterized by the steps of: receiving the signals at an electronic processor that is coupled to the one or more electrodes; executing, by the electronic processor, an automated set-up routine that processes the signals to automatically provide at least some set-up results for new mapping configurations; and processing the signals, by the electronic processor, with beat detection and beat acceptance criteria for existing mapping configurations to provide information about how well the signals match one or more of the existing mapping configurations.

Example 11 is the method of Example 10, wherein the steps of executing the automated set-up routine and processing the signals with the beat detection and beat acceptance criteria for the existing maps are performed in parallel.

Example 12 is the method of any of Examples 10 and 11, including displaying information about the degree of matching between the signals and a current mapping configuration of the existing mapping configurations and displaying information about the degree of matching between the signals and at least one other mapping configuration of the existing mapping configurations.

Example 13 is the method of any of Examples 10-12, including updating the new mapping configurations in response to changes in the signals and displaying updated new mapping configurations.

Example 14 is the method of any of Examples 10-13, including switching from mapping the signals using one of the existing mapping configurations to mapping the signals using another one of the existing mapping configurations or one of the new mapping configurations.

Example 15 is the method of any of Examples 10-14, including determining which of the new mapping configurations and the existing mapping configurations more closely matches the signals and determining which of the new mapping configurations and the existing mapping configurations are redundant.

Example 16 is a system for providing information about a patient's heart. The system includes one or more electrodes that receive signals from electrical activity of the heart over one or more heart beat cycles and an electronic processor coupled to the one or more electrodes. In some embodiments, the electronic processor is to receive the signals from the one or more electrodes, execute an automated set-up routine that processes the signals to automatically provide at least some set-up results for new mapping configurations, and process the signals with beat detection and beat acceptance criteria for the new or existing mapping configurations to provide information about how well the signals match one or more of the new or existing mapping configurations. In some embodiments, the electronic processor is to receive the signals from the one or more electrodes and execute an automated set-up routine that processes the signals to automatically provide at least some set-up results for new mapping configurations. In some embodiments, the electronic processor is to receive the signals from the one or more electrodes and process the signals with beat detection and beat acceptance criteria for the new or existing mapping configurations to provide information about how well the signals match one or more of the new or existing mapping configurations.

Example 17 is the system of Example 16, wherein the electronic processor executes the automated set-up routine and processes the signals with the beat detection and beat acceptance criteria for the existing mapping configurations in parallel.

Example 18 is the system of Example 16, wherein the electronic processor executes the automated set-up routine at one or more of a predetermined time interval, once every heart beat cycle, and once per second.

Example 19 is the system of Example 16, wherein the automated set-up routine provides the new mapping configurations in response to changes in the signals and the new mapping configurations are updated and displayed while matching the signals to one or more of the new or existing mapping configurations.

Example 20 is the system of Example 16, including a user interface, wherein the degree of matching between the signals and at least two of the new or existing mapping configurations is displayed on the user interface.

Example 21 is the system of Example 16, including a user interface, wherein information for making a determination about which of the new or existing mapping configurations most closely matches the signals is displayed on the user interface.

Example 22 is the system of Example 16, including a user interface for switching from mapping the signals using one of the existing mapping configurations to mapping the signals using another one of the existing mapping configurations or one of the new mapping configurations.

Example 23 is the system of Example 16, wherein the electronic processor determines which of the new mapping configurations and the existing mapping configurations are redundant.

Example 24 is the system of Example 16, wherein the electronic processor automatically switches from mapping the signals using one of the existing mapping configurations to mapping the signals using another one of the existing mapping configurations or one of the new mapping configurations.

Example 25 is a system for providing information about a patient's heart. The system including one or more electrodes that receive signals from electrical activity of the heart over one or more heart beat cycles and an electronic processor coupled to the one or more electrodes. The electronic processor is to receive the signals from the one or more electrodes, execute an automated set-up routine that processes the signals to automatically provide at least some set-up results for new mapping configurations, and process the signals with beat detection and beat acceptance criteria for existing mapping configurations to provide information about how well the signals match the existing mapping configurations, wherein the electronic processor executes the automated set-up routine and processes the signals with the beat detection and beat acceptance criteria for the existing mapping configurations in parallel. The system also includes a user interface, wherein information for making a determination about which of the existing mapping configurations more closely matches the signals is displayed on the user interface.

Example 26 is the system of Example 25, wherein the automated set-up routine provides the new mapping configurations in response to changes in the signals and the new mapping configurations are updated and displayed on the user interface.

Example 27 is the system of Example 25, wherein the degree of matching between the signals and a current mapping configuration of the existing mapping configurations is displayed on the user interface while mapping the signals to a current map associated with the current mapping configuration and the degree of matching between the signals and at least one other mapping configuration of the existing mapping configurations is displayed on the user interface while mapping the signals to the current map.

Example 28 is the system of Example 25, wherein a user can switch from mapping the signals using a current mapping configuration of the existing mapping configurations to mapping the signals using another one of the existing mapping configurations or one of the new mapping configurations via the user interface.

Example 29 is the system of Example 25, wherein the electronic processor is configured to automatically switch from mapping the signals using a current mapping configuration of the existing mapping configurations to mapping the signals using another one of the existing mapping configurations or one of the new mapping configurations.

Example 30 is a method for providing information about a patient's heart. The method including receiving signals from electrical activity of the heart over one or more heart beat cycles at one or more electrodes, receiving the signals at an electronic processor that is coupled to the one or more electrodes, executing, by the electronic processor, an automated set-up routine that processes the signals to automatically provide at least some set-up results for new mapping configurations, and processing the signals, by the electronic processor, with beat detection and beat acceptance criteria for existing mapping configurations to provide information about how well the signals match one or more of the existing mapping configurations.

Example 31 is the method of Example 30, wherein executing the automated set-up routine and processing the signals with the beat detection and beat acceptance criteria for the existing maps is performed in parallel.

Example 32 is the method of Example 30, including displaying information about the degree of matching between the signals and a current mapping configuration of the existing mapping configurations and displaying information about the degree of matching between the signals and at least one other mapping configuration of the existing mapping configurations.

Example 33 is the method of Example 30, including updating the new mapping configurations in response to changes in the signals and displaying updated new mapping configurations.

Example 34 is the method of Example 30, including switching from mapping the signals using one of the existing mapping configurations to mapping the signals using another one of the existing mapping configurations or one of the new mapping configurations.

Example 35 is the method of Example 30, including determining which of the new mapping configurations and the existing mapping configurations more closely matches the signals and determining which of the new mapping configurations and the existing mapping configurations are redundant.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

During cardiac mapping of multiple different types of cardiac rhythms, mixed in time, the cardiac rhythm may change spontaneously or due to some intentional act, such as pacing of the heart. When this occurs, it is useful to quickly determine whether the new cardiac rhythm matches an existing mapping configuration. If the new cardiac rhythm matches an existing mapping configuration, the data being acquired can be added to an existing cardiac map or to a new cardiac map associated with the matching mapping configuration. If the new cardiac rhythm does not match an existing mapping configuration, a new cardiac mapping configuration can be configured and the data can be added to a new cardiac map or to an existing cardiac map, using the new cardiac mapping configuration.

The present disclosure describes embodiments of systems and methods for quickly determining whether a new cardiac rhythm matches an existing mapping configuration and for quickly configuring a new cardiac mapping configuration, thereby potentially maximizing mapping data collection and reducing frustration.

Figure 1:
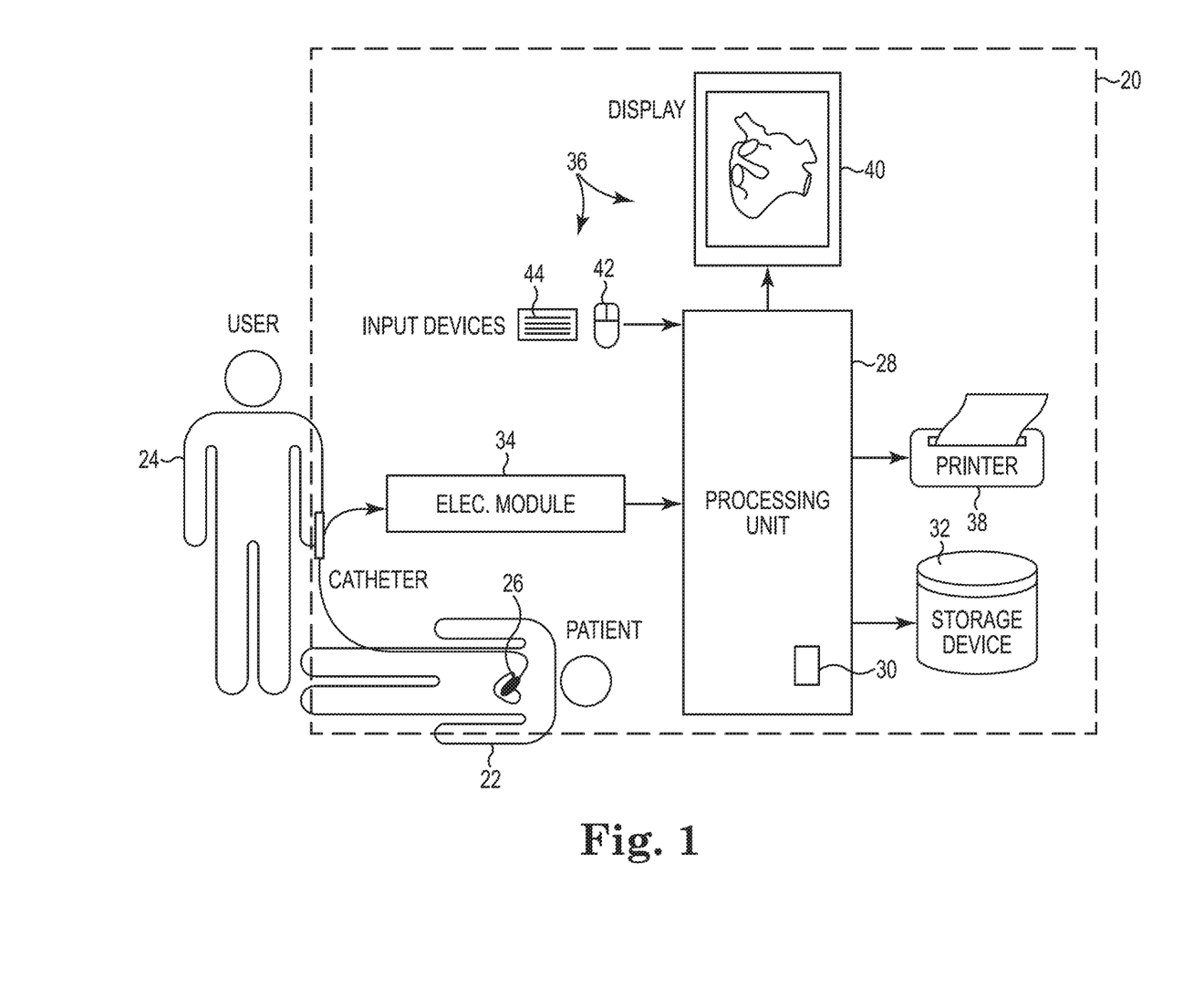
FIG. 1 is a diagram illustrating an electro-anatomical mapping system for mapping multiple different types of cardiac rhythms, which are mixed in time, according to embodiments of the disclosure.

FIG. 1 is a diagram illustrating an electro-anatomical mapping system 20 for mapping multiple different types of cardiac rhythms, which are mixed in time, of a patient 22, according to embodiments described in the disclosure. The system 20 provides information for determining whether a new cardiac rhythm has been previously mapped using an existing cardiac mapping configuration and information for configuring a new cardiac mapping configuration. Using an existing mapping configuration or a new mapping configuration, the data associated with the new cardiac rhythm can be added to an existing cardiac map or to a new cardiac map. With this information, a user 24 of the system 20, such as a physician and/or a technician, and/or the system 20 itself, can quickly switch to using either an existing cardiac mapping configuration that matches the new cardiac rhythm or to a new cardiac mapping configuration.

The system 20 includes a catheter 26 having one or more electrodes. During a signal acquisition stage, the catheter 26 can be displaced to multiple locations within the heart chamber of interest into which the catheter 26 is inserted. In some embodiments, the catheter 26 is configured for contact mapping. In some embodiments, the catheter 26 is configured for near-contact mapping. In some embodiments, the catheter 26 is configured for non-contact mapping. In embodiments, the electrodes are mounted on the catheter 26 following a three dimensional olive shape, where the electrodes are mounted on a device capable of deploying the electrodes into the desired shape while inside the heart and capable of retracting the electrodes when the catheter is removed from the heart. To allow deployment into the three dimensional shape, the electrodes may be mounted on a balloon or shape memory material, such as Nitinol. In embodiments, the catheter 26 may include any number of electrodes arranged according to any desired shape.

In embodiments, the system 20 includes other catheters and/or electrodes for measuring the electrical activity of the heart. These electrodes can be externally mounted on or near the patient for measuring the electrical activity of the heart. For example, the system 20 can include electrocardiogram (ECG or EKG) leads that are used to measure the electrical activity of the heart. The system 20 can use the signals obtained from the ECG leads for system functions, such as determining which new or existing mapping configuration(s) more closely matches a cardiac rhythm and switching to using a different mapping configuration for adding data to an associated cardiac map.

At each of the locations to which the catheter 26 is moved, the catheter's one or more electrodes acquire signals resulting from the electrical activity of the heart. This provides, to the user 24, physiological data pertaining to the heart's electrical activity based on information acquired at multiple locations, which may facilitate, for example, providing a relatively accurate reconstruction of the physiological behavior of the endocardium surface. The acquisition of signals at multiple catheter locations in the heart chamber enables the catheter 26 to effectively act as a "megacatheter" whose effective number of electrodes and electrode span is proportional to the product of the number of locations in which signal acquisition is performed and the number of electrodes on the catheter 26. In some embodiments of non-contact mapping, to enhance the quality of the physiological information at the endocardium surface, the catheter 26 is moved to more than three locations, such as more than 5, 10, or even 50 locations, within the heart chamber. Further, the spatial range over which the catheter is moved may be larger than one third (⅓) of the diameter of the heart cavity, such as larger than 35%, 40%, 50% or even 60% of the diameter of the heart cavity.

In embodiments, the physiological information is computed based on signals measured over several heart beats, either at a single catheter location within the heart chamber or over several locations. In circumstances where physiological information is based on multiple measurements over several heart beats, the measurements can be synchronized with one another so that the measurements are performed, and/or analyzed, with respect to approximately the same phase of the heart cycle. Also, the signal measurements over multiple beats can be synchronized based on features detected from physiological data, such as, for example, a surface electrocardiogram (ECG) or an intracardiac electrogram (EGM).

The system 20 includes a processing unit 28, which may be, or include, a processor that executes code stored in internal memory 30 and/or in a storage device 32 to perform operations, according to embodiments of the disclosure. The internal memory 30 and/or the storage device 32 also, or alternatively, may store data acquired by the one or more electrodes of the mapping catheter 26. In some embodiments, the internal memory 30 and/or the storage device 32 may store data acquired via other catheters and or external electrodes, such as via ECG leads. In some embodiments, the processing unit 28 is an electronic processor, which may be, at least in part, a software processor.

The processing unit 28 is communicatively coupled to the catheter 26 and receives the signals from the one or more electrodes. The processing unit 28 executes, from memory such as the internal memory 30 and/or the storage device 32, an automated set-up routine that processes the signals from the one or more electrodes to determine new mapping configurations and may provide at least some set-up information and/or set-up results for the new mapping configurations to the user 24. Also, the processing unit 28 executes, from memory such as the internal memory 30 and/or the storage device 32, code that processes the signals with beat detection and beat acceptance criteria for one or more existing mapping configurations. In some embodiments, the existing mapping configurations include a current existing mapping configuration being used to add data to an associated current existing cardiac map and one or more other existing mapping configurations. This provides information about how well the signals match the existing mapping configurations.

In some embodiments, the processing unit 28 executes a reconstruction procedure to determine the physiological information at the endocardium surface. To expedite embodiments of computational operations performed by the system 20, the processing unit 28 may compute, prior to the insertion of the catheter 26 into the heart chamber and/or before signal acquisition by the catheter's electrodes has commenced, transformation functions that can be used, during a mapping procedure, to facilitate the reconstruction process. Once the catheter 26 is inserted and displaced to a particular location in the heart chamber, the mapping procedure may be performed expeditiously by computing those transformation components that were not computed ahead of the signal acquisition stage, and combining those components with the appropriate pre-processed transformation components to obtain the overall transformation function(s). The overall transformation function may be applied to the acquired raw data to perform an inverse reconstruction operation.

The processing unit 28 may also perform a catheter registration procedure. The location of the catheter 26 inserted into the heart chamber may be determined using a conventional sensing and tracking system (not shown) that provides the three dimensional spatial coordinates of the catheter 26 and/or its multiple electrodes with respect to the catheter's coordinate system as established by the sensing and tracking system. However, to perform the mapping procedure and/or reconstruct physiological information on the endocardium surface, it may be desirable to align the coordinate system of the catheter 26 with the endocardium surface's coordinate system. The processing unit 28 or another processing module of the system 20 may be configured to determine a coordinate system transformation function that transforms the three dimensional spatial coordinates of the catheter's locations into coordinates expressed in terms of the endocardium surface's coordinate system, or vice-versa. In some embodiments, the processing unit 28 performs post-processing operations on the reconstructed physiological information to extract and display useful features of the information to the operator of the system 20 and/or other persons, such as a physician.

The signals acquired by the one or more electrodes of the catheter 26 may be passed to the processing unit 28 via a signal conditioning module 34 that receives the signals from the catheter 26 and performs signal enhancement operations on the signals before they are forwarded to the processing unit 28. Signal conditioning hardware may be used to amplify, filter, and sample intracardiac potential measured by one or more electrodes. In some embodiments, for example, the intracardiac signals have maximum amplitudes of 60 mV and mean amplitudes of a few millivolts. In some embodiments the signals are bandpass filtered in a frequency range, such as 0.5-500 Hz, and sampled with analog to digital converters, such as converters with 15-bit resolution at 1 kHz.

To avoid interference with electrical equipment in the room, the signals may be filtered to remove one or more frequencies corresponding to the equipment. Other types of signal processing operations may be implemented, such as, for example, spectral equalization, automatic gain control, and/or the like. The resultant processed signals are forwarded by the module 34 to the processing unit 28 for further processing.

The system 20 includes a user interface 36 and, optionally, peripheral devices, such as a printer 38, which are communicatively coupled to the processing unit 28. The user interface 36 includes one or more display devices 40 and input devices, such as a mouse 42 and a keyboard 44. The user interface 36 may receive signals from the processing unit 28 and display information about which existing mapping configuration(s) more closely matches a current cardiac rhythm. In some embodiments, the user interface 36 may receive signals from the processing unit 28 and display information about whether a current cardiac rhythm more closely matches a current existing mapping configuration being used to add data to an associated current existing cardiac map or a different existing mapping configuration. Also, the user interface 36 may display information about a new mapping configuration obtained via the automated set-up routine. In some embodiments, with the user interface 32 displaying this information, the user 24 can quickly and easily determine which mapping configuration of the existing mapping configurations and the new mapping configuration more closely matches the cardiac rhythm such that it can be used to add data to an associated cardiac map, including either an existing cardiac map or a new cardiac map. Also, in some embodiments, the user interface 32 can be used to switch to using one of the existing mapping configurations or a new mapping configuration. In embodiments, the user interface 36 displays this information while the system 20 is adding signals into the current cardiac map. In some embodiments, the user interface 36 includes a graphical user interface that includes a touch screen, which can be used for switching from using one of the existing mapping configurations to using another one of the existing mapping configurations or a new mapping configuration and adding the data to an associated cardiac map that can be an existing cardiac map or a new cardiac map.

Figure 2:
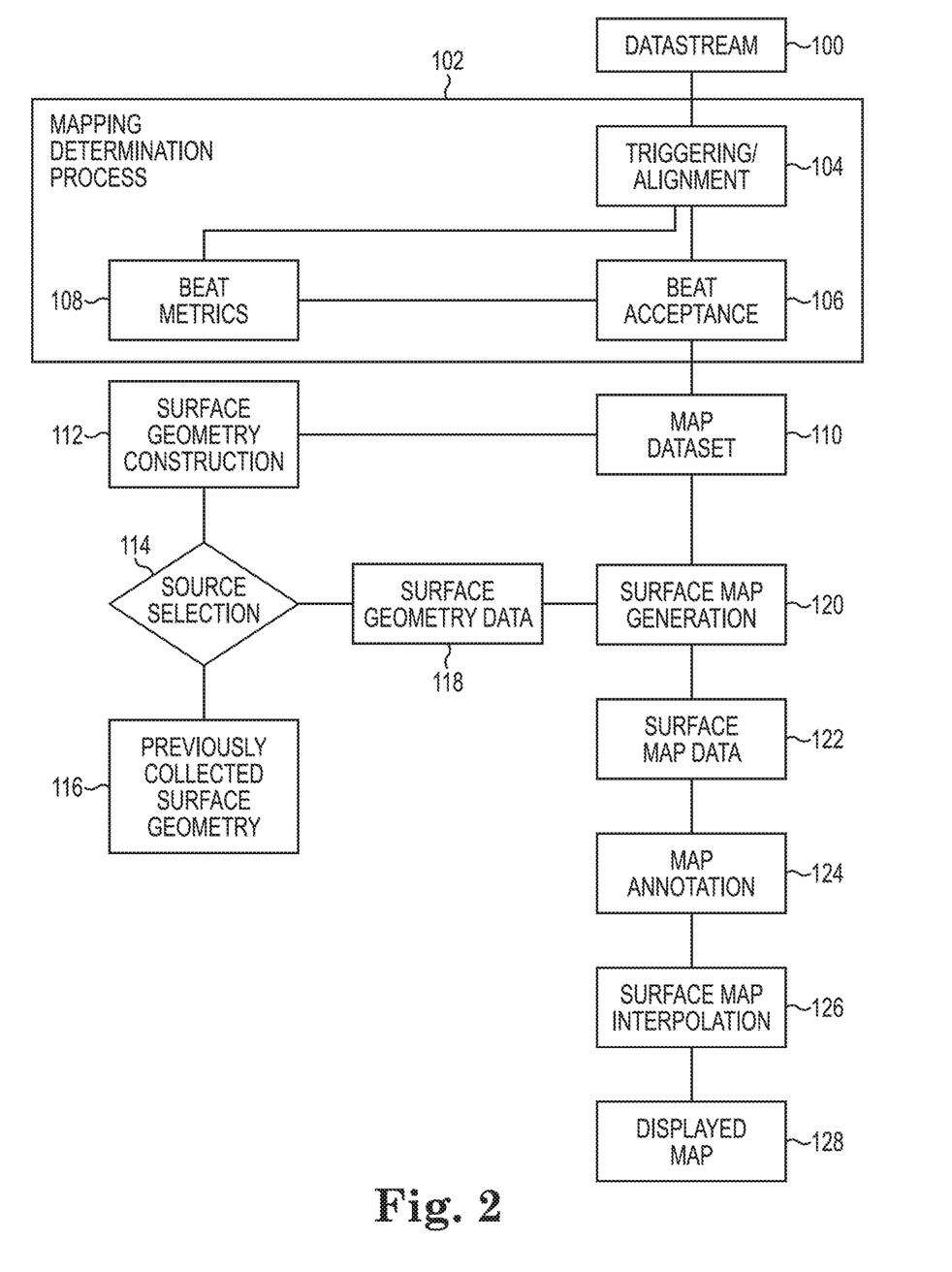
FIG. 2 is a flowchart diagram illustrating an automated electro-anatomical mapping process, according to embodiments of the disclosure.

FIG. 2 is a flowchart diagram illustrating an automated electro-anatomical mapping process, according to embodiments described in the disclosure. The electro-anatomical mapping process of FIG. 2 may be performed, at least in part, by the electro-anatomical mapping system 20 of FIG. 1. In some embodiments, the processing unit 28 executes computer code stored in the internal memory 30 and/or storage device 32 to facilitate the electro-anatomical mapping process of FIG. 2.

In the electro-anatomical mapping process of FIG. 2, a data stream 100 containing multiple signals is input into the system (e.g., the mapping system 20 depicted in FIG. 1). The data stream 100 provides a collection of physiological and non-physiological signals and information that serve as inputs to the mapping process. The data stream 100 may include signals received from one or more electrodes on the catheter 26. Also, the data stream 100 may include signals and/or information such as unipolar or bipolar intracardiac EGM signals, ECG signals, electrode and/or catheter location information originating from a variety of methodologies including magnetic, impedance, ultrasound, fluoroscopy, and real time magnetic resonance imaging (MRI) methodologies, tissue proximity information, catheter force or contact information such as from force spring sensing, piezoelectric sensing, and optical sensing, catheter tip and/or tissue temperature, acoustic information, catheter electrical coupling information, respiration phase, blood pressure, and/or other physiological information. In addition, the data stream 100 may contain information such as catheter shape and electrode properties. The signals and information can be collected directly by the mapping system and/or obtained from another system using an analog or digital interface.

A mapping determination process 102 receives the data stream 100 and processes the data to provide information for determining whether the acquired signals in the data stream 100 should be added to the current map, another existing cardiac map, or a new cardiac map. The mapping determination process 102 processes the data with beat detection and beat acceptance criteria for the current mapping configuration and for one or more other existing mapping configurations to provide information about how well the incoming data matches the current mapping configuration and the other existing mapping configurations. Also, the mapping determination process 102 automatically determines new mapping configurations for the incoming data, which may include determining at least some set-up information and/or set-up results for the new mapping configurations. In some embodiments, the mapping determination process 102 determines the new mapping configurations in parallel with processing the data with the beat detection and the beat acceptance criteria of the existing mapping configurations, where in parallel can be by serially switching between determining the new mapping configurations and processing the data with the beat detection and the beat acceptance criteria of the existing mapping configurations. In embodiments, the mapping determination process 102 continuously (or continually) processes the data or signals with beat detection and beat acceptance criteria of the existing mapping configurations such as by sequentially comparing different beat detection and beat acceptance criteria to the incoming data. In embodiments, the mapping determination process 102 continuously (or continually) determines new mapping configurations for the incoming data, such as by analyzing predetermined time intervals of data. In embodiments, the mapping determination process 102 continuously (or continually) determines new mapping configurations for the incoming data by processing the data at one or more of a predetermined time interval, once every heart beat cycle, and once per second.

The mapping determination process 102 processes the data with beat detection and beat acceptance criteria to provide information about how well the signals match the existing mapping configurations, including existing mapping configurations associated with existing cardiac maps. In embodiments, the mapping determination process 102 processes the data with beat detection and beat acceptance criteria for the current mapping configuration associated with a current existing maps into which the data are currently being added, and with beat detection and beat acceptance criteria for one or more other existing mapping configurations. In embodiments, the mapping determination process 102 processes the data with beat detection and beat acceptance criteria for all existing cardiac mapping configurations.

In some embodiments, the mapping determination process 102 displays the degree of matching between the incoming data and the existing mapping configurations via a user interface, such as the user interface 36. The mapping determination process 102 may display the degree of matching for determining whether the cardiac rhythms of the incoming data have been previously mapped and to determine which of the existing mapping configurations more closely matches the incoming data. The mapping determination process 102 may also, or alternatively, display, on the user interface, information such as set-up information for a new mapping configuration for the cardiac rhythm. With this information displayed on the user interface, the user may quickly and easily determine whether the incoming data should continue to be added to the current map, or added to another existing map or a new cardiac map. In embodiments, the mapping determination process 102 displays at least some of the above information on the user interface while using the current mapping configuration of the existing mapping configurations to add incoming data to the associated current map.

In some embodiments of the mapping determination process 102 and the generation of cardiac maps, one or more of the signals in the incoming data may be used as a reference for triggering and alignment 104 of the data stream 100 relative to the cardiac rhythm of the incoming data, another biological cycle, and/or an asynchronous system clock. The triggering and alignment 104 defines a time instance around which a window of data from the data stream 100 is sampled. In embodiments, a trigger event is detected from a physiological signal designated as a reference signal. The trigger event may be asynchronous to the patient and derived from a system clock. For example, when constructing an activation map it is common to use an ECG or EGM signal as a reference, and when constructing an anatomical shell, a system clock may provide the trigger events.

Also, when aggregating data from multiple cardiac beats to create an electro-anatomical map, it may be useful to trigger based on a stable reference in the data stream 100. In that case, the reference provides alignment across beats to a desired phase in the cardiac cycle. In embodiments, a single signal source is selected for triggering, such as ECG lead II, and waveform attributes such as minimum/maximum, absolute maximum, maximum/minimum slope, and/or first deviation from baseline may be used to detect a trigger. According to embodiments, using multiple signals to determine triggering can provide various advantages in comparison to triggering schemes based on a single signal.

The triggering and alignment 104 of the signals results in beat datasets at 104, and a number of beat metrics 108 are computed for each of the beat datasets at 104. The beat metrics 108 may be computed using information from a single signal spanning one or more beats, over multiple signals within the same beat, and/or from multiple signals spanning multiple beats. The beat metrics 108 provide multiple types of information on the quality of a beat dataset at 104 and the likelihood that the beat data in the beat dataset is acceptable for inclusion in a map dataset 110. After the beat metrics 108 are computed, a beat acceptance process 106 aggregates the criteria and decides whether a beat dataset can be added to a particular map dataset 110. In embodiments, a number of map datasets 110 may be created, where each map dataset 110 corresponds to a different existing cardiac map.

As indicated previously, in embodiments, the mapping determination process 102 is configured to indicate a degree of matching between the incoming data and one or more of the existing mapping configurations, which include beat detection and beat acceptance criteria that are used to analyze the incoming data. Also, the mapping determination process 102 may provide a new mapping configuration for the incoming data. A user, e.g., user 24, and/or the system, e.g., system 20, can determine, based at least in part on the degree of matching, whether to 1) continue using a current mapping configuration to continue adding data to the associated current map; 2) switch to using another one of the existing mapping configurations and add data to the current map, another existing map or a new map; or 3) switch to using a new mapping configuration and add data to the current map, another existing map or a new map. In embodiments, for example, the mapping determination process 102 indicates the degree of matching between the incoming data and at least one of the existing cardiac mapping configurations by displaying the percentage of beat datasets at 104 that match each of the existing mapping configurations over a predetermined period of time. In some embodiments, for example, the mapping determination process 102 indicates the degree of matching between the incoming data and at least one of the existing cardiac mapping configurations by displaying the percentage of beat datasets at 104 that can be added into each of the different map datasets 110 over a predetermined period of time. In some embodiments, metrics other than the percentage of beat datasets at 104 that match each of the existing mapping configurations over a predetermined period of time or the percentage of beat datasets at 104 that can be added into each of the different map datasets 110 over a predetermined period of time can be used to to indicate the degree of matching. In some embodiments, metrics that use a subset of the beat acceptance criteria can be used to indicate the degree of matching.

The automated electro-anatomical mapping process of FIG. 2 continues with a surface map generation process 120 that is employed to generate surface map data from the map datasets 110 and surface geometry data 118. In embodiments, the surface geometry data 118 may be generated concurrently, or at least during the same data acquisition process, using identical or different triggering and beat acceptance metrics employing a surface geometry construction process 112. The surface geometry construction process 112 may construct surface geometry using data such as electrode locations and catheter shape contained in the data stream 100. Also, previously collected surface geometry 116 may be used as an input to the surface map data. Such surface geometry 116 may be collected in the same procedure using a different map dataset or using a different modality such as CT, MRI, ultrasound, and/or rotational angiography, which is registered to the catheter locating system.

A system, such as system 20, may select the source of the surface geometry data at 114 and provide surface geometry data 118 to the surface map generation process 120. The generation process 120 generates surface map data 122 that may provide information on cardiac electrical excitation, cardiac motion, tissue proximity information, tissue impedance information, force information, and/or any other collected and/or derived information. Once obtained, the surface map data 122 may be further processed to annotate desired features from the underlying data, a process defined herein as surface map annotation 124. Desired annotations may include instantaneous potential, activation time, voltage amplitude, dominant frequency and/or other properties of the signal. Once computed, the annotations may be displayed superimposed on chamber geometry. If the number of annotations is lower than the number of elements that make up the display of surface geometry, surface map interpolation 126 may be employed. Displayed maps 128 may be computed and displayed separately, combined, and/or overlaid on top of each other.

Figure 3:
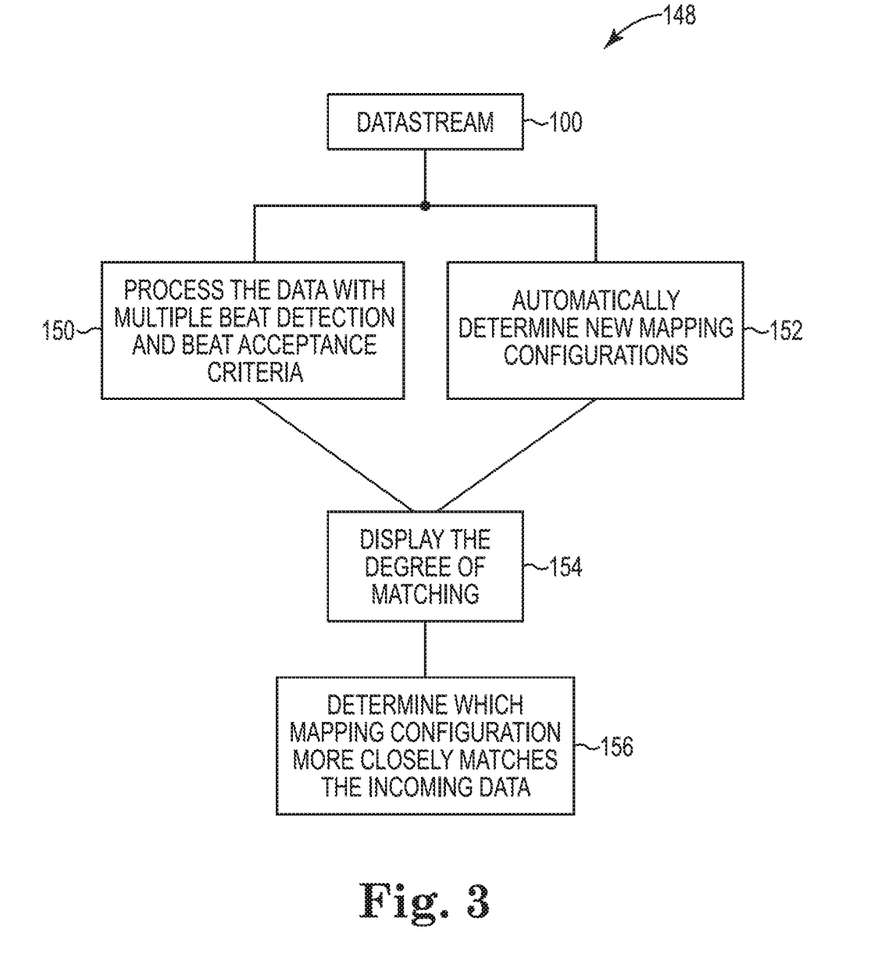
FIG. 3 is a diagram illustrating a process for determining which mapping configuration more closely matches the cardiac rhythm signals, according to embodiments of the disclosure.

FIG. 3 is a diagram illustrating a process 148 for determining which mapping configuration more closely matches the incoming cardiac rhythm signals, according to embodiments of the disclosure. In some embodiments, the process 148 is part of the mapping determination process 102 that is part of the electro-anatomical mapping process of FIG. 2.

The process 148 receives the data stream 100 and processes data, such as signals and information, in the data stream 100 to provide information for determining which mapping configuration of the existing mapping configurations more closely matches the incoming data stream 100 and information for a new mapping configuration. The process 148 provides parallel processing paths for the data in the data stream 100.

At 150, the process 148 processes the data with multiple beat detection and beat acceptance criteria for the existing mapping configurations, which can include a current mapping configuration and one or more other existing mapping configurations. For example, in system 20, the processing unit 28 may execute, from memory such as the internal memory 30 and/or the storage device 32, code that processes the signals with the beat detection and beat acceptance criteria for the current mapping configuration that is used to add data to the current existing cardiac map and for one or more other existing mapping configurations that may or may not have been used to add data to an existing cardiac map. This processing provides information about how well the incoming data matches the current mapping configurations and the one or more other existing mapping configurations. In embodiments, the process 148 processes the data with beat detection and beat acceptance criteria for all existing mapping configurations. In some embodiments, the process 148 continuously (or continually) processes the data with the beat detection and beat acceptance criteria of existing mapping configurations, such as by sequentially comparing different beat detection and beat acceptance criteria to the incoming data.

At 152, the process 148 automatically determines new mapping configurations for at least a portion of the incoming data, which includes determining at least some set-up information and/or set-up results for the new mapping configurations. For example, in system 20, the processing unit 28 may execute, from memory such as the internal memory 30 and/or the storage device 32, the automated set-up routine that processes signals from one or more electrodes to determine new mapping configurations and provide at least some set-up information and/or set-up results for the new mapping configurations to the user 24.

In the process 148, the automated set-up routine can be configured to operate in a number of different ways. In an example, the automated set-up routine can be configured to use automatically selected parameters, such as predetermined default parameters to, at least, begin determining the new mapping configuration. In another example, the automated set-up routine can be configured to use multiple parameters and/or iteratively changing the parameters to determine the best matching mapping configuration for the incoming data. Also, in embodiments, after the automated set-up routine has determined a suggested new mapping configuration, the process 148 provides signals or other data to the user, which enables the user to validate or modify the suggested new mapping configuration. Embodiments of the system display data that indicates a percentage of the datasets of the incoming data that would be accepted using the new mapping configuration.

In embodiments, in the process 148, the automated set-up routine runs continually and, in a given time interval, provides many new mapping configurations. Each new mapping configuration is slightly or significantly different than previously determined new mapping configurations. In some embodiments, the automated set-up routine combines a number of these previously determined new mapping configurations to come up with a new mapping configuration that can be checked against the incoming data. In some embodiments, the automated set-up routine averages a number of these previously determined new mapping configurations to come up with a new mapping configuration that can be checked against the incoming data. In some embodiments, the automated set-up routine analyzes the sequence of previously determined new mapping configuration to determine a new mapping configuration.

As illustrated in FIG. 3, the process 148 determines the new mapping configurations in parallel with processing the data with the beat detection and the beat acceptance criteria of the existing mapping configurations. In some embodiments, the process 148 continuously (or continually) determines new mapping configurations for the incoming data, such as by analyzing predetermined time intervals of data. In some embodiments, the process 148 continuously (or continually) determines new mapping configurations for the incoming data by processing the data at one or more of a predetermined time interval, once every heartbeat, and once per second.

At 154, the process 148 displays the degree of matching between the incoming data and the existing mapping configurations via a user interface, such as the user interface 36. The process 148 displays the degree of matching to facilitate determining whether the type of cardiac rhythm in the incoming data has been previously mapped and to facilitate determining which of the existing mapping configurations more closely matches the incoming data. In embodiments, the process 148 also displays information about the new cardiac mapping configuration, including set-up information for the new cardiac mapping configuration for the cardiac rhythm. For example, in system 20, the user interface 36 may receive signals from the processing unit 28 and display the information about whether a current cardiac rhythm more closely matches the current mapping configuration or a different existing mapping configuration. Also, the user interface 36 may display information about the new mapping configuration determined by the automated set-up routine. In some embodiments, the process 148 indicates the degree of matching between the incoming data and at least one of the existing cardiac maps, by displaying the percentage of beat datasets that more closely matches each of the existing mapping configurations over a predetermined period of time. In some embodiments, the process 148 indicates the degree of matching between the incoming data and at least one of the existing cardiac maps, by displaying the percentage of beat datasets that can be mapped into each of the different map datasets 110 over a predetermined period of time. In some embodiments, metrics other than the percentage of beat datasets that more closely matches each of the existing mapping configurations over a predetermined period of time or the percentage of beat datasets that can be mapped into each of the different map datasets 110 over a predetermined period of time can be used to to indicate the degree of matching. In some embodiments, metrics that use a subset of the beat acceptance criteria can be used to indicate the degree of matching. In embodiments, the process 148 displays at least some of the above information on the user interface while adding incoming data to a current map.

In embodiments, at 154, the process 148 determines which mapping configurations, including new and existing mapping configurations, are effectively identical or sufficiently similar to be considered interchangeable. The process 148 then analyzes the mapping configurations and determines which mapping configurations to show to the user. In some embodiments, the process 148 prioritizes the mapping configurations for display to the user, where prioritizing can depend on factors such as which mapping configurations are the best match to the incoming data, which are the most recently used, and/or which are the most different from one another.

At 156, a user, such as user 24, determines which mapping configuration more closely matches the incoming data. The user and/or the system determines whether to 1) continue using a current mapping configuration to continue adding data to the associated current map, 2) switch to using another one of the existing mapping configurations and add data to the current map, another existing map or a new map, or 3) switch to using a new mapping configuration and add data to the current map, another existing map or a new map. The user analyzes the displayed information and can select a different mapping configuration and a different cardiac map, such as by using a mouse or a keyboard or a touchscreen. Also, in some embodiments, the system 20, using a set of heuristic rules, automatically determines which mapping configuration to use and, if needed, switches to adding the incoming data into a different map.

Figure 4:
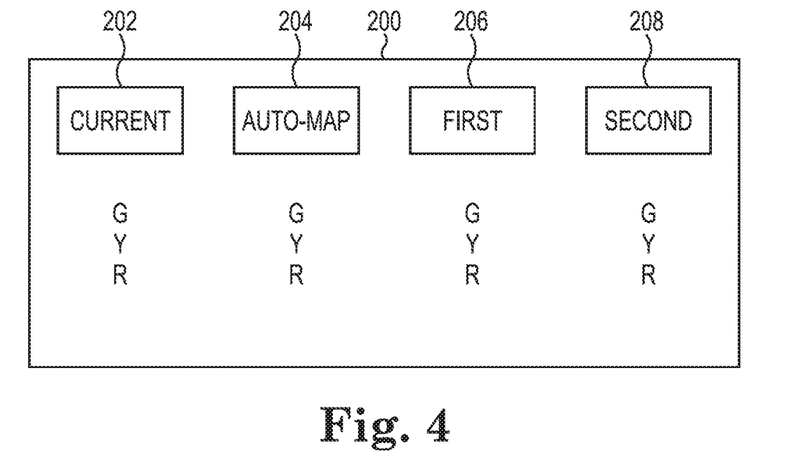
FIG. 4 is a diagram illustrating a user interface display that displays a degree of matching between incoming data and three existing cardiac mapping configurations, according to embodiments of the disclosure.

FIG. 4 is a diagram illustrating a user interface display 200 that displays the degree of matching between the incoming data and three existing cardiac mapping configurations, according to embodiments of the disclosure. The display 200 displays results for the current mapping configuration and two other existing mapping configurations. In embodiments, the display 200 can be configured to display results for any number of existing mapping configurations such as, for example, one existing mapping configuration, two existing mapping configurations, three existing mapping configurations, four existing mapping configurations, five existing mapping configurations, and/or the like. As shown in FIG. 4, embodiments of the display 200 include a current mapping configuration result display 202, an auto-map (automated set-up routine) display 204, a first existing mapping configuration result display 206, and a second existing mapping configuration result display 208. In some embodiments, the first and second existing mapping configuration result displays 206 and 208 display information for the two existing cardiac mapping configurations, other than the current mapping configuration, that have (or would have if they were the current map) the highest beat dataset acceptance rates, such as acceptance of the most beat datasets in a predetermined time period. In some embodiments, the display 200 displays at least the current mapping configuration result display 202 and the first existing mapping configuration result display 206. In some embodiments, the predetermined time period is a value such as, for example, 10 seconds.

The current mapping configuration result display 202 provides an indication of the beat dataset acceptance rate of the current mapping configuration. The first existing mapping configuration result display 206 provides an indication of what the beat dataset acceptance rate would be for the first existing mapping configuration, and the second existing map result display 208 provides an indication of what the beat dataset acceptance rate would be for the second existing mapping configuration.

In some embodiments, the current mapping configuration result display 202, the first existing mapping configuration result display 206, and the second existing mapping configuration result display 208, display colors to indicate the beat dataset acceptance rates. For example, the displays can be color coded to display green (G), yellow (Y), or red (R), where green indicates an acceptable acceptance rate, yellow a lower acceptance rate than green and a higher acceptance rate than red, and red an unacceptable acceptance rate. In some embodiments, for example, a green acceptance rate is greater than or equal to 60%, a red acceptance rate is less than or equal to 40%, and a yellow acceptance rate is between 40 and 60%. In some embodiments, other ranges for assigning acceptance categories may be used, other indicators for indicating ranges of beat acceptance rates may be used, and/or the like. For example, instead of, or in addition to, colors, embodiments may utilize shapes (e.g., a number of horizontal bars such as those commonly used to indicate network signal strength), sounds, symbols, and/or combinations of these.

In some embodiments, one or more of the current mapping configuration result display 202, the first existing mapping configuration result display 206, and the second existing mapping configuration result display 208, display percentages that indicate the acceptance rate for the corresponding cardiac mapping configuration. In other embodiments, a different number of colors, other suitable colors, and/or other acceptance rate percentages for the different colors can be used for displaying the degree of matching between the incoming data and the existing cardiac maps, including the current map.

In some embodiments, the auto-map (automated set-up routine) display 204 provides one or more visual indications such as, for example, colors to indicate whether a new cardiac mapping configuration is ready or satisfactory for use. For example, the display may be color coded to display green, yellow, or red, where green indicates a new cardiac mapping configuration has been configured and is ready for use, yellow indicates that the new cardiac mapping configuration may not be ready for use, and red indicates the new cardiac mapping configuration is not ready for use. In some embodiments, a green display indicates that greater than or equal to 60% of the beat datasets would be accepted by the new cardiac mapping configuration, a yellow indicates that between 40 and 60% of the beat datasets would be accepted by the new cardiac mapping configuration, and a red indicates that less than or equal to 40% of the beat datasets would be accepted by the new cardiac mapping configuration. In some embodiments, the auto-map display 204 displays percentages that indicate what the acceptance rate would be for the new cardiac mapping configuration. In other embodiments, a different number of colors, other suitable colors, other acceptance rate percentages and/or ranges for the different colors, different indicators such as, for example, shapes, sounds, symbols, and/or the like may be used.

In one example, assuming that the predetermined time period for determining acceptance rates is 10 seconds and that one beat dataset is provided per second, then 10 beat datasets are provided during a 10 second time period. Also, assuming that the cardiac rhythm has been steady for greater than 10 seconds and that all beat datasets during the most recent 10 second interval have been added to the current map, then the current mapping configuration result display 202 might be green and/or display 100%, the auto-map display 204 might be green and/or display 100%, and the first and second existing mapping configuration result displays 206 and 208 might be red and/or display 0%. In addition, the percentages given for color changes in the preceding paragraphs are used in this example.

To begin, according to this example, the cardiac rhythm changes, and the first new beat dataset is not added to the current map. Instead, the first new beat dataset would be added to the map associated with the first existing mapping configuration. Thus, only 9 out of the last 10 beat datasets have been added to the current map and the current mapping configuration result display 202 will remain green and/or display 90%, the first existing mapping configuration result display 206 will remain red and/or display 10%, the second existing mapping configuration result display 208 will remain red and/or display 0%, and the auto-map display 204 will remain green and/or display 90%.

Assuming that the cardiac rhythm remains as previously changed, the new beat datasets are not added to the current map but would be mapped into the map associated with the first existing mapping configuration and not the map associated with the second existing mapping configuration. Thus, after a second new beat dataset, the current mapping configuration result display 202 will remain green and/or display 80%, the first existing mapping configuration result display 206 will remain red and/or display 20%, the second existing mapping configuration result display 208 will remain red and/or display 0%, and the auto-map display 204 will remain green and/or display 80%. At this point, the user would likely continue mapping into the current map using the current mapping configuration.

After third and fourth new beat datasets, the current mapping configuration result display 202 will remain green and/or display 60%, the first existing mapping configuration result display 206 will remain red and/or display 40%, the second existing mapping configuration result display 208 will remain red and/or display 0%, and the auto-map display 204 will remain green and/or display 60%. At this point, the user would likely continue adding data to the current map using the current mapping configuration, but may notice the change in acceptance percentages.

After a fifth new beat dataset, the current mapping configuration result display 202 will turn yellow and/or display 50%, the first existing mapping configuration result display 206 will also turn yellow and/or display 50%, the second existing mapping configuration result display 208 will remain red and/or display 0%, and the auto-map display 204 will turn yellow and/or display 50%. At this point, the user may start to look for a different cardiac mapping configuration and the user will likely notice that the first existing mapping configuration result display 206 has turned yellow.

After a sixth new beat dataset, the current mapping configuration result display 202 will turn red and/or display 40%, the first existing mapping configuration result display 206 will turn green and/or display 60%, the second existing mapping configuration result display 208 will remain red and/or display 0%, and the auto-map display 204 will turn red and/or display 40%. At this point, the user will see that the first existing mapping configuration is likely the next cardiac mapping configuration to be selected. Also, at this point, the automated set-up routine may determine a new cardiac mapping configuration based on five or six new beat datasets.

After the seventh or more new beat datasets, the current mapping configuration result display 202 will remain red and/or display 30% or less, the first existing mapping configuration result display 206 will remain green and/or display 70% or more, and the second existing mapping configuration result display 208 will remain red and/or display 0%. If the automated set-up routine determines a new cardiac mapping configuration based on the five or six new beat datasets, the auto-map display 204 will turn green and/or display 70% or more. At this point, the user will likely switch to the first existing mapping configuration, which is then used as the new current mapping configuration, and the process continues.

In another example, assuming that the predetermined time period for determining acceptance rates is 10 seconds and that one beat dataset is provided per second, then 10 beat datasets are provided during a 10 second time period. Also, assuming that the cardiac rhythm has been steady for greater than 10 seconds and that all beat datasets during the most recent 10 second interval have been added to the current map, then the current mapping configuration result display 202 will be green and/or display 100%, the auto-map display 204 will be green and/or display 100%, and the first and second existing mapping configuration result displays 206 and 208 will be red and/or display 0%. In addition, the percentages given for the color changes in the preceding paragraphs are used for the color changes in this example.

To begin, the cardiac rhythm changes, and the first new beat dataset is not added to the current map or to either of the maps associated with the first and second existing mapping configurations. Instead, the first new beat dataset is part of a completely new cardiac rhythm. Thus, only 9 out of the last 10 beat datasets have been added to the current map and the current mapping configuration result display 202 will remain green and/or display 90%, the first existing mapping configuration result display 206 will remain red and/or display 0%, the second existing mapping configuration result display 208 will remain red and/or display 0%, and the auto-map display 204 will remain green and/or display 90%.

Assuming that the cardiac rhythm remains as previously changed, the new beat datasets will not be added into the current map or to either of the maps associated with the first and second existing mapping configurations. Thus, after second, third, and fourth new beat datasets, the current mapping configuration result display 202 will remain green and/or display 60%, the first existing mapping configuration result display 206 will remain red and/or display 0%, the second existing mapping configuration result display 208 will remain red and/or display 0%, and the auto-map display 204 will remain green and/or display 60%. At this point, the user would likely continue adding data to the current map.

After a fifth new beat dataset, the current mapping configuration result display 202 will turn yellow and/or display 50%, the first existing mapping configuration result display 206 will remain red and/or display 0%, the second existing mapping configuration result display 208 will remain red and/or display 0%, and the auto-map display 204 will turn yellow and/or display 50%. At this point, the user can start looking for a different cardiac mapping configuration and will notice that the auto-map display 204 has turned yellow.

After a sixth new beat dataset, the current mapping configuration result display 202 will turn red and/or display 40%, the first existing mapping configuration result display 206 will remain red and/or display 0%, the second existing mapping configuration result display 208 will remain red and/or display 0%, and the auto-map display 204 will turn red and/or display 40%. At this point, the user will see that the auto-map display 204 has turned red and the automated set-up routine may determine a new cardiac mapping configuration based on five or six new beat datasets.

After the seventh or more new beat datasets, the current mapping configuration result display 202 will remain red and/or display 30% or less, the first existing mapping configuration result display 206 will remain red and/or display 0%, and the second existing mapping configuration result display 208 will remain red and/or display 0%. If the automated set-up routine determines a new cardiac mapping configuration based on five or six new beat datasets, the auto-map display 204 will turn green and/or display 70% or more. At this point, the user will likely switch to adding the data into a map associated with the new cardiac mapping configuration determined by the automated set-up routine, which then becomes the new current mapping configuration, and the process continues.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A system for providing information about a patient's heart, comprising: one or more electrodes that receive signals from electrical activity of the heart over one or more heart beat cycles; and an electronic processor coupled to the one or more electrodes to: receive the signals from the one or more electrodes; execute an automated set-up routine that processes the signals to automatically provide one or more set-up result for new mapping configurations; and process the signals with beat detection and beat acceptance criteria for the new mapping configurations or existing mapping configurations to provide information about matching the signals to one or more of the new mapping configurations or the existing mapping configurations, wherein the electronic processor determines which of the new mapping configurations and the existing mapping configurations are redundant.

2. The system of claim 1, wherein the electronic processor executes the automated set-up routine and processes the signals with the beat detection and the beat acceptance criteria for the existing mapping configurations in parallel.

3. The system of claim 1, wherein the electronic processor executes the automated set-up routine at one or more of a predetermined time interval, once every heart beat cycle, and once per second.

4. The system of claim 1, wherein the automated set-up routine provides the new mapping configurations in response to changes in the signals and the new mapping configurations are updated and displayed while matching the signals to one or more of the new mapping configurations or the existing mapping configurations.

5. The system of claim 1, wherein the electronic processor is configured to process the signals to provide the new mapping configurations or the existing mapping configurations to map beats of multiple, different types of cardiac rhythms in the signals to new cardiac maps or existing cardiac maps of the multiple, different types of cardiac rhythms.

6. The system of claim 1, comprising:
a user interface, wherein a degree of matching between the signals and at least two of the new mapping configurations or the existing mapping configurations is displayed on the user interface.

7. The system of claim 1, comprising:
a user interface, wherein information for determining which of the new mapping configurations or the existing mapping configurations most closely matches the signals is displayed on the user interface.

8. The system of claim 1, comprising:
a user interface for switching from mapping the signals using one of the existing mapping configurations to mapping the signals using another one of the existing mapping configurations or one of the new mapping configurations.

9. The system of claim 1, wherein the electronic processor automatically switches from mapping the signals using one of the existing mapping configurations to mapping the signals using another one of the existing mapping configurations or one of the new mapping configurations.

10. A system for providing information about a patient's heart, comprising:
one or more electrodes that receive signals from electrical activity of the heart over one or more heart beat cycles;
an electronic processor coupled to the one or more electrodes to: receive the signals from the one or more electrodes;
execute an automated set-up routine that processes the signals to automatically provide one or more set-up result for new mapping configurations; and process the signals with beat detection and beat acceptance criteria for existing
mapping configurations to provide information about matching the signals to the existing mapping configurations, wherein the electronic processor executes the automated set-up routine and processes the signals with the beat detection and the beat acceptance criteria for the existing mapping configurations in parallel and the electronic processor is configured to determine which of the new mapping configurations and the existing mapping configurations are redundant; and a user interface, wherein information for determining which of the existing mapping configurations more closely matches the signals is displayed on the user interface.

11. The system of claim 10, wherein the automated set-up routine provides the new mapping configurations in response to changes in the signals and the new mapping configurations are updated and displayed on the user interface.

12. The system of claim 10, wherein a first degree of matching between the signals and a current mapping configuration of the existing mapping configurations is displayed on the user interface while mapping the signals to a current map associated with the current mapping configuration and a second degree of matching between the signals and at least one other mapping configuration of the existing mapping configurations is displayed on the user interface while mapping the signals to the current map.

13. The system of claim 10, wherein a user can switch from mapping the signals using a current mapping configuration of the existing mapping configurations to mapping the signals using another one of the existing mapping configurations or one of the new mapping configurations via the user interface.

14. The system of claim 10, wherein the electronic processor is configured to automatically switch from mapping the signals using a current mapping configuration of the existing mapping configurations to mapping the signals using another one of the existing mapping configurations or one of the new mapping configurations.

15. A method for providing information about a patient's heart, comprising:
receiving signals from electrical activity of the heart over one or more heart beat cycles at one or more electrodes;
receiving the signals at an electronic processor that is coupled to the one or more electrodes;
executing, by the electronic processor, an automated set-up routine that processes the signals to automatically provide one or more set-up result for new mapping configurations;
processing the signals, by the electronic processor, with beat detection and beat acceptance criteria for existing mapping configurations to provide information about matching the signals to one or more of the new mapping configurations or the existing mapping configurations; and determining, by the electronic processor, which of the new mapping configurations and the existing mapping configurations are redundant.

16. The method of claim 15, wherein executing the automated set-up routine and processing the signals with the beat detection and the beat acceptance criteria for the existing maps is performed in parallel.

17. The method of claim 15, comprising: displaying information about a first degree of matching between the signals and a current mapping configuration of the existing mapping configurations; and displaying information about a second degree of matching between the signals and at least one other mapping configuration of the existing mapping configurations.

18. The method of claim 15, comprising:
updating the new mapping configurations in response to changes in the signals; and displaying updated new mapping configurations.

19. The method of claim 15, comprising:
switching from mapping the signals using one of the existing mapping configurations to mapping the signals using another one of the existing mapping configurations or one of the new mapping configurations.

20. The method of claim 15, wherein executing the automated set-up routine comprises executing the automated set-up routine at one or more of a predetermined time interval, once every heart beat cycle, and once per second.

* * * * *